United States Patent [19]

Prost-Marechal et al.

[11] 4,202,835
[45] May 13, 1980

[54] PREPARATION OF α-CYANO-3-PHENOXY-BENZYL ALCOHOL

[75] Inventors: Jacques Prost-Marechal, Paris; Jean Tessier, Vincennes, both of France

[73] Assignee: Roussel Uclaf, Paris, France

[21] Appl. No.: 28,994

[22] Filed: Apr. 11, 1979

Related U.S. Application Data

[63] Continuation of Ser. No. 820,097, Jul. 29, 1977, abandoned.

[30] Foreign Application Priority Data

Aug. 27, 1976 [FR] France .................. 76 25938

[51] Int. Cl.² .......................... C07C 121/75
[52] U.S. Cl. .................. 260/465 F; 260/512 C
[58] Field of Search ...................... 260/465 F

[56] References Cited
U.S. PATENT DOCUMENTS 3,987,079 10/1976 Kay et al. .................. 260/465 F Primary Examiner—Dolph H. Torrence
Attorney, Agent, or Firm—Hammond & Littell, Weissenberger and Muserlian

[57] ABSTRACT

A novel process for the preparation of α-cyano-3-phenoxy-benzyl alcohol comprising reacting a compound capable of generating $CN^-$ ions and a m-phenoxy benzaldehyde bisulfite of the formula

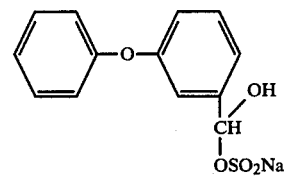

in the presence of a solvent or mixture of solvents which alcohol is useful for preparing insecticidal esters of cyclopropane carboxylic acids with a dihalovinyl chain.

11 Claims, No Drawings

PREPARATION OF α-CYANO-3-PHENOXY-BENZYL ALCOHOL

PRIOR APPLICATION

This application is a continuation of our copending, commonly assigned U.S. Pat. application Ser. No. 820,097 filed July 29, 1977 and now abondoned.

STATE OF THE ART

Houben-Weyl, Methods of Organic Chemistry, Vol. VIII/III, p. 276–277 describes the preparation of nitriles by action of an alkali metal cyanide and a bisulfite of an aldehyde. DT-OS No. 2,231,312 describes the preparation of α-cyano-3-phenoxy-benzylic alcohol by reacting sodium cyanide and m-phenoxy-benzaldehyde in an acid medium.

OBJECTS OF THE INVENTION

It is an object of the invention to provide a novel process for the preparation of α-cyano-3-phenoxy-benzyl alcohol in excellent yields.

This and other objects and advantages of the invention will become obvious from the following detailed description.

THE INVENTION

The novel process of the invention for the preparation of α-cyano-3-phenoxy-benzyl alcohol comprises reacting a compound capable of generating CN$^-$ ions and a m-phenoxy benzaldehyde bisulfite of the formula

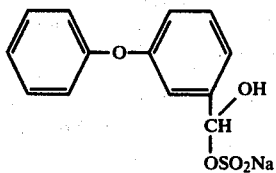

in the presence of a solvent or mixture of solvents.

Examples of compounds capable of generating cyanide ions are hydrogen cyanide, ammonium cyanide, alkali metal cyanides such as potassium cyanide and sodium cyanide and alkaline earth metal cyanides such as calcium cyanide. The preferred compounds are alkali metal cyanides.

The reaction is preferably effected in an aqueous medium and if a mixture of solvents is used, it is preferably water and an aprotic dipolar solvent such as dimethylformamide, dimethoxy ethane, dimethyl sulfoxide or acetonitrile. The preferred reaction medium is a mixture of water and dimethylformamide.

The reaction of the invention is preferably effected in the presence of an acidic agent. The acid agent may be a strong acid such as sulfuric acid or hydrochloric acid but is a carboxylic acid of weak acidity. The reaction is preferably effected in an aqueous medium in the presence of acetic acid although other lower alkanoic acids may be used.

In a preferred mode of the process of the invention a suspension of the combination bisulfite of m-phenoxy-benzaldehyde is introduced into an aqueous sodium cyanide solution. In another preferred embodiment, an aqueous solution of sodium cyanide is added to a suspension of the combination bisulfite of m-phenoxy-benzaldehyde in dimethylformamide followed by addition of acetic acid.

The reaction may also be effected in an anhydrous medium and the reactant is preferably anhydrous alkali metal cyanide. The solvent or solvent mixture for this reaction is preferably at least one anhydrous aprotic dipolar solvent such as dimethylformamide, dimethoxyethane, dimethylsulfoxide or acetonitrile. The preferred solvent is anhydrous dimethylformamide, preferably without the addition of an acid agent. An anhydrous weak acid agent such as acetic acid may, however, be used.

An advantageous mode of the process comprises adding an anhydrous alkali metal cyanide to an anhydrous suspension of the combination bisulfite of m-phenoxy-benzaldehyde in dimethylformamide.

The combination bisulfite of m-phenoxy-benzaldehyde has proven to be very useful for the preparation of α-cyano-3-phenoxy-benzyl alcohol and may be prepared by reaction of an alkali metal bisulfite and m-phenoxy-benzaldehyde in a solvent or mixture of solvents such as water, isopropyl ether and methanol mixture or a mixture of water and isopropanol.

The combination bisulfite of m-phenoxy-benzaldehyde presents with the isolated aldehyde the advantage of being more stable and is purifiable by crystallization from an organic solvent such as ethyl acetate. The purified product is obtained in excellent degree of purity, on the order of 98% and is converted into a α-cyano-3-phenoxy-benzyl alcohol in practically quantitative yields.

In the following examples there are described several preferred embodiments to illustrate the invention. However, it should be understood that the invention is not intended to be limited to the specific embodiments.

EXAMPLE 1

A solution of 200 g of sodium metabisulfite in 800 ml of water was added to a solution of 200 g of m-phenoxy-benzaldehyde in 800 ml of isopropyl ether and after the addition of 250 ml of methanol, the mixture was stirred for 3 hours and was vacuum filtered. The recovered precipitate was washed with 1—1 water-methanol mixture and then with isopropyl ether and was dried to obtain 295 g of the combination bisulfite of m-phenoxy-benzaldehyde (titer of 95.5% mobile hydrogen). The product was crystallized from 4 volumes of ethyl acetate to obtain a 97.6% yield of the product with a titer of mobile hydrogen of 98%.

20 g of the said bisulfite were added over one minute under a nitrogen atmosphere to 40 ml of dimethylformamide and the resulting suspension was stirred for 15 minutes at 20° C. and was then cooled to 5° C. A solution of 5.4 g of potassium cyanide in 20 ml of water were added to the mixture over 20 minutes at a temperature below 10° C. and the mixture was stirred for 2 hours at 5° C. and was then filtered. 100 ml of water and 100 ml of ethyl acetate were added to the filtrate and the mixture was stirred and decanted. The aqueous phase with extracted with 100 ml of ethyl acetate and the combined ethyl acetate extracts were washed with water, dried and evaporated to dryness under reduced pressure. The residue was dissolved in ether and the ether solution was washed with water, dried and evaporated to dryness to obtain 14.46 g of α-cyano-3-phenoxy-benzyl alcohol.

EXAMPLE 2

A solution of 0.765 Kg of sodium cyanide in 3.8 liters of water was added with stirring at 5° C. over 10 minutes to a mixture of 3.700 Kg of combination bisulfite of m-phenoxy-benzaldehyde (98% titer) in 7.4 liters of dimethylformamide and 3.8 liters of acetic acid were added thereto over 30 minutes at 5° C. The mixture was stirred for 30 minutes at 10° C. and the reaction mixture was then poured into a mixture of water and ethyl acetate. The mixture was stirred and decanted and the aqueous phase was extracted twice more with ethyl acetate. The combined ethyl acetate phases were washed with water, dried and stirred with 0.37 Kg of activated charcoal and 0.37 Kg of sodium sulfate. The mixture was filtered and the filtrate was evaporated to dryness under reduced pressure to obtain 2.770 Kg of α-cyano-3-phenoxy-benzyl alcohol containing 1% of dimethylformamide.

The product had a titer of 6.3 g of nitrogen per 100 g (6.20-theoretical) and 100% of mobile hydrogen titer. For storage, 13.5 ml of acetic acid were added thereto.

EXAMPLE 3

20 g of anhydrous combination bisulfite of m-phenoxy-benzaldehyde were added under an inert atmosphere to 80 ml of anhydrous dimethylformamide and then 3.3 g of anhydrous sodium cyanide were added thereto at 0° C. under an inert atmosphere. The mixture was stirred at 0° C. for 45 minutes after which a sample of the reaction mixture was taken to verify by chromatography analysis that the conversion was complete. The reaction mixture was poured into a mixture of ice, water, acetic acid and isopropyl ether and the mixture was stirred and decanted. The aqueous phase was extracted with isopropyl ether and the combined organic phases were washed with water, dried and evaporated to dryness to obtain 13.8 g of α-cyano-3-phenoxy-benzyl alcohol.

Various modifications of the process of the invention may be made without departing from the spirit or scope thereof and it is to be understood that the invention is intended to be limited only as defined in the appended claims.

We claim:

1. A process for the preparation of α-cyano-3-phenoxy-benzyl alcohol comprising reacting a compound capable of generating CN⁻ ions and a m-phenoxy-benzaldehyde bisulfite of the formula

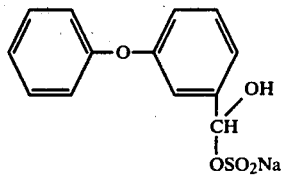

in the presence of at least one aprotic dipolar organic solvent.

2. The process of claim 1 wherein the cyanide generating compound is an alkali metal cyanide.

3. The process of claim 1 wherein the solvent also contains water and acetic acid.

4. The process of claim 3 wherein the solvent is a mixture of water and dimethylformamide.

5. The process of claim 1 wherein the reaction is effected in the presence of an acid agent.

6. The process of claim 1 wherein a suspension of combination bisulfite of m-phenoxy-benzaldehyde in the aprotic dipolar solvent is introduced into an aqueous solution of sodium cyanide.

7. The process of claim 1 wherein an aqueous solution of sodium cyanide is added to a suspension of combination bisulfite of m-phenoxy-benzaldehyde in dimethylformamide followed by addition of acetic acid.

8. The process of claim 1 wherein the reaction is effected under anhydrous conditions.

9. The process of claim 9 wherein the solvent is anhydrous dimethylformamide.

10. The process of claim 9 wherein anhydrous alkali metal cyanide is added to an anhydrous suspension of combination bisulfite of m-phenoxy-benzaldehyde in dimethylformamide.

11. The process of claim 1 wherein the aprotic dipolar solvent is selected from the group consisting of dimethylformamide, dimethoxyethane, dimethylsulfoxide and acetonitrile.

* * * * *